US00PP09505P

United States Patent [19]

Hvid

[11] Patent Number: Plant 9,505

[45] Date of Patent: Apr. 9, 1996

[54] BEGONIA PLANT NAMED 'BERLIN'

[75] Inventor: Soren Hvid, Aarup, Denmark

[73] Assignee: L. Daehnfeld A/S, Odense, Denmark

[21] Appl. No.: 384,547

[22] Filed: Feb. 7, 1995

[51] Int. Cl.[6] ..... A01H 5/00

[52] U.S. Cl. ..... Plt./87.18

[58] Field of Search ..... Plt./87.18

*Primary Examiner*—James R. Feyrer

*Attorney, Agent, or Firm*—Foley & Lardner

[57] ABSTRACT

A new cultivar of Begonia named 'Berlin' characterized by a compact growth habit with excellent branching; simple, alternate, dark green, double-serrated foliage that is ovate to orbicular and pink flowers on a sturdy peduncle with 15 or more tepals.

1 Drawing Sheet

The present invention relates to a new and distinctive cultivar of Begonia plant, botanically known as *Begonia hiemalis* (Fotsch), and known by the cultivar name 'Berlin.'

The new cultivar 'Berlin' is the product of a planned breeding program. The female or seed parent was a proprietary tuberous Begonia selection designated Code No. 40489-57 and the male or pollen parent was a proprietary selection of *B. socotrana* designated Code No. 109. 'Berlin' was asexually propagated for the first time in February 1990 in Marslev, Denmark. Continuous asexual propagation by tip cuttings has demonstrated that the combination of characteristics as herein disclosed for the new cultivar 'Berlin' are firmly fixed and are retained through successive generations of asexual reproduction.

The following characteristics distinguish the new begonia from both its parents and other Begonias commercially known and used in the floriculture industry:

1. Flower color of 'Berlin' is less purple than 'Barbara' (U.S. Plant Pat. No. 5,179) and is slightly lighter pink than 'Chantilly' (U.S. Plant Pat. No. 6,434), 'Karita' (U.S. Plant Pat. No. 5,746) and 'Imke' (U.S. Plant Pat. No 5,539). Flower color of 'Berlin' is lighter and more red than 'Guinevere' (U.S. Plant Pat. No. 6,435) and 'Fantasia' (U.S. Plant Pat. No. 7,259) and slightly darker than 'Elfe' (U.S. Plant Pat. No. 4,125).

2. The underside of young foliage of 'Berlin' is maroon while that of 'Barbara' is light green; that of 'Imke' is slightly red and that of 'Fantasia' is light green.

3. The flowers of 'Berlin' are double but generally have fewer tepals than those of 'Chantilly', 'Guinevere' and 'Fantasia.'

4. The tepals of 'Berlin' are not ruffled like those of 'Chantilly', 'Guinevere' and 'Fantasia.'

5. The habit of 'Berlin' is upright in contrast to the pendulous habit of 'Fantasia.'

6. 'Berlin' is more compact than 'Barbara' or 'Karita.'

7. The foliage of 'Berlin' is more sharply serrated than that of 'Karita.'

8. The underside of the mature foliage of 'Berlin' does not have a heavy infusion of red-purple like that of 'Elfe.'

'Berlin' has not been tested under all available environmental conditions and the phenotype may vary with variations in environmental conditions such as temperature, light intensity, daylength and humidity without a change in the genotype of the plant variety.

The accompanying colored photograph taken August 1993 illustrates the overall appearance of the cultivar taken as an oblique view of the plant in 12 cm plastic pot and showing the colors as true as it is reasonably possible to obtain in a colored reproduction of this type.

The following is a detailed description of the new Begonia cultivar based on plants produced under commercial practices in Hannover, Germany and Ashtabula, Ohio. Color references are made to the Royal Horticultural Society Colour Chart (RHS) except where general terms of ordinary dictionary significance are used.

Parentage: *Begonia×tuberhybrida* designated Code No. 40489-57 as the seed parent and *Begonia socotrana* designated Code No. 109 as the pollen parent.

Propagation:

*Type cutting.*—Tip cutting 3 to 4 cm long.

*Time to root.*—28–35 days at 22°–24° C. summer; 35–42 days at 20°–22° C. winter.

*Rooting habit.*—Abundant, fibrous.

Plant description:

*Form.*—Compact, self-supporting herbaceous, close internodes.

*Habit of growth.*—Compact, excellent branching when pinched, early flowering.

*Foliage.*—Simple, alternate, dark green, double-serrated but not deeply cut. Size: 5–7 cm wide and 7 to 9 cm long. Shape: Generally ovate to orbicular, apices nearly acute, base unequal cordate. Texture: Glabrous; leathery. Margin: Doubly serrated, but not cut deep. Color: The topside of young foliage is 146B RHS with 183C RHS infusion. The underside of young foliage is 183C RHS with the exception of the veins which are 146C RHS. The topside of mature foliage is 139A RHS while the underside is 146B. Veination: Palmate.

Flowering description:

*Flowering habits.*—Indeterminate, early to flower with short days, longer to flower with long days. Flowers borne upright, not pendulous. Flowers are fully double.

*Natural flowering season.*—Year round, initiating earlier under short day conditions.

*Flowers borne.*—Flowers borne on a sturdy peduncle.

*Tepals.*—Color: The topside of the outer tepals in winter when opening is 52C-D RHS and the topside of the inner tepals is 52C RHS. The underside of the tepals is 52C RHS. Number of tepals: 15 or more. Size of flowers: 5 to 6.5 cm.

*Reproductive organs.*—Pistils: None. Stamen: None.

I claim:

1. A new and distinct cultivar of Begonia named 'Berlin,' as illustrated and described.

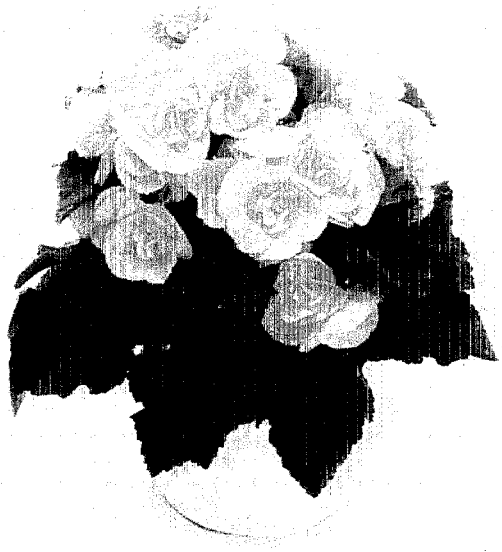

* * * * *